United States Patent
Shea et al.

(10) Patent No.: US 7,211,192 B2
(45) Date of Patent: May 1, 2007

(54) HYBRID ORGANIC-INORGANIC ADSORBENTS

(75) Inventors: Kenneth J. Shea, Irvine, CA (US); Stephen T. Hobson, Gunpowder, MD (US); Joseph Tran, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 413 days.

(21) Appl. No.: 10/112,573

(22) Filed: Mar. 29, 2002

(65) Prior Publication Data

US 2003/0176396 A1 Sep. 18, 2003

Related U.S. Application Data

(63) Continuation-in-part of application No. 09/872,097, filed on Jun. 1, 2001, now Pat. No. 6,417,236.

(60) Provisional application No. 60/280,711, filed on Mar. 30, 2001, provisional application No. 60/209,337, filed on Jun. 2, 2000.

(51) Int. Cl.
*B01D 11/00* (2006.01)

(52) U.S. Cl. .................. 210/634; 210/640; 210/660; 210/690

(58) Field of Classification Search ............... 210/634, 210/640, 660, 690
See application file for complete search history.

(56) References Cited

U.S. PATENT DOCUMENTS 5,414,192 A    5/1995 Lansbarkis 6,417,236 B1    7/2002 Hobson et al.

FOREIGN PATENT DOCUMENTS

IT    13040173 B1    12/1998

OTHER PUBLICATIONS

Mercier et al., "Access in Mesoporous Materials: Advantages of a Uniform Pore Structure in the Design in a Heavy Metal Ion Adsorbent for Environmental Remediation", *Adv. Mater.* 1997, 9, No. 6, pp. 500-503.
Small et al., "Arylene-and alkylene-bridged polysilsesquioxanes", *Journal of Non-Crystalline Solids* 160 (1993) 234-246.
Wu et al., "Preparation of Disolfides by the Oxidation of Thiols Using Bromine", *Synthetic Communications* 26(1), 191-196 (1996).

(Continued)

*Primary Examiner*—Samuel Barts
(74) *Attorney, Agent, or Firm*—Orrick, Herrington & Sutcliffe, LLP

(57) ABSTRACT

The present invention relates generally to hybrid organic-inorganic adsorbents for decontamination of fluids. Bridged poysilsesquioxanes are a family of hybrid organic-inorganic materials prepared by sol-gel processing of monomers that contain a variable organic bridging group and two or more trifunctional silyl groups. Specifically, the present invention relates to dipropylenedisulfide-co-phenylene-bridged polysilsesquioxane compositions, methods of making dipropylenedisulfide-co-phenylene-bridged polysilsesquioxanes, and methods of use of dipropylenedisulfide-co-phenylene-bridged polysilsesquioxanes. The present invention discloses properties of dipropylenedisulfide-co-phenylene-bridged polysilsesquioxanes that include high ligand loading, increased surface area, and increased porosity. These properties make dipropylenedisulfide-co-phenylene-bridged polysilsesquioxanes excellent adsorbents for decontamination of fluids for use in environmental and industrial processes.

16 Claims, 5 Drawing Sheets

Interconversion of disulfide and thiol functionality.

OTHER PUBLICATIONS

Kresge et al., "Ordered mesoporous molecular sieves synthesized by a liquid-crystal template mechanism", *Nature*, vol. 359 (Oct. 22, 1992), pp. 710-712.

Buder et al., "Synthesis and Spectroscopy of Silylsulfanes", *Z. Naturforsch*, 34b, pp. 790-793 (Mar. 16, 1979).

Mercier et al., "Heavy Metal Ion Adsorbents Formed by the Grafting of a Thiol Functionality to Mesoporous Silica Molecular Sieves: Factors Affecting Hg(II) Uptake", *Environ. Sci. Technol.*, vol. 32, No. 18 (1998), pp. 2749-2754.

Feng et al., "Functionalized Monolayers on Ordered Mesoporous Supports", *Science*, vol. 276 (1997), pp. 923-926.

Beck et al., "A New Family of Mesoporous Molecular Sieves Prepared with Liquid Crystal Templates", *J. Am. Chem. Soc.* (1992), vol. 114, pp. 10834-10843.

Liu et al., "Hybrid Mesoporous Materials with Functionalized Monolayers", *Adv. Mater.* (1998), vol. 10, No. 2, pp. 161-165.

Liu et al., "Hybrid Mesoporous Materials with Functionalized Monolayers", *Chem. Eng. Technol.* (1998), vol. 21, No. 1, pp. 97-100.

Raman et al., "Template-Based Approaches to the Preparation of Amorphous, Nanoporous Silicas", *Chem. Mater.* (1996) vol. 8, pp. 1682-1701.

Shea et al., Bridged Polysilsesquioxanes, Molecular-Engineered Hybrid Organica-Inorganic Materials *Chem. Mater.* (2001), vol. 13, pp. 3306-3319.

Shea et al., "Arylsilsesquioxane Gels and Related Materials. New Hybrids of Organic and Inorganic Networks", *J. Am. Chem. Soc.* (1992), vol. 114, pp. 6700-6710.

Humphrey et al., "Reduction of Aromatic Disulfides with Triphenylphosphine", *Analytical Chemistry* (Aug. 1994), vol. 36, No. 9, pp. 1812-1814.

Humphrey et al., "Reduction of Disulfides with Tributylphosphine", *Analytical Chemistry* (Jan. 1965), vol. 37, No. 1, pp. 164-165.

Shea et al., "Bridged Polysilsesquioxanes. Molecular-Engineered Hybrid Organic-Inorganic Materials", *Chem. Mater.* (2001), vol. 13, pp. 3306-3319.

Tran, Joseph Anh, "Synthesis and characterization of organically-bridged polysilsesquioxanes: New hybrid organic-inorganic syntehetic glasses", Published 1999 Thesis (Ph.D., Chemistry), University of California, Irvine (1999), Chapter 5, pp. 180-221.

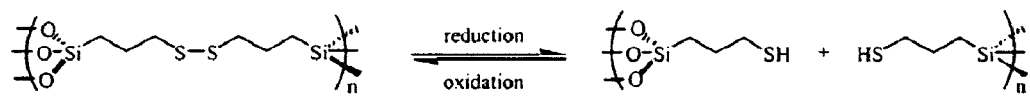
Figure 1: Interconversion of disulfide and thiol functionality.

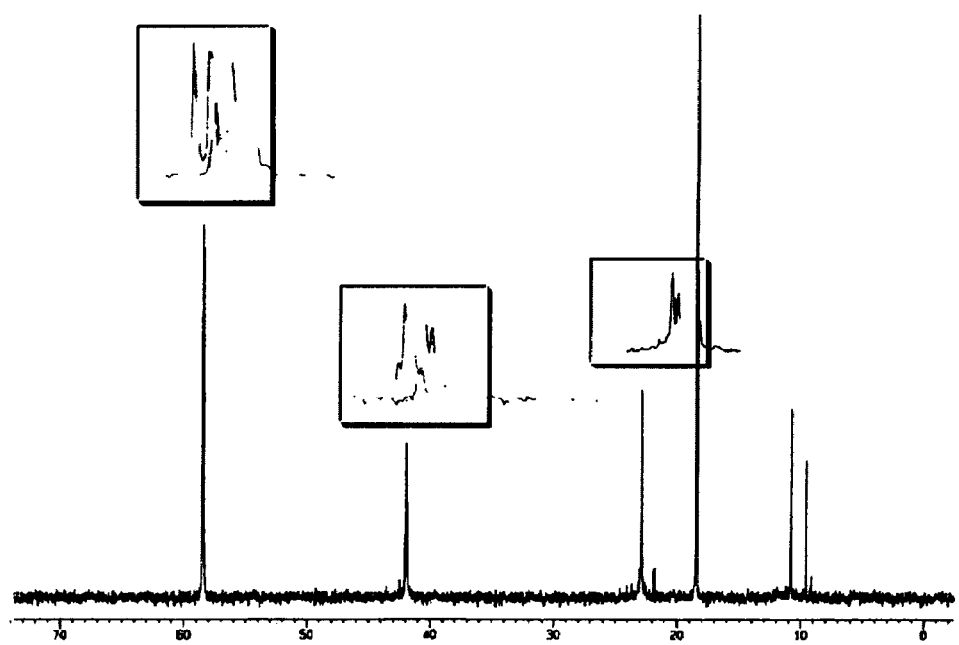
Figure 2: $^{13}$C NMR of bis(3-triethoxysilylpropyl)disulfide using bromine as the oxidant.

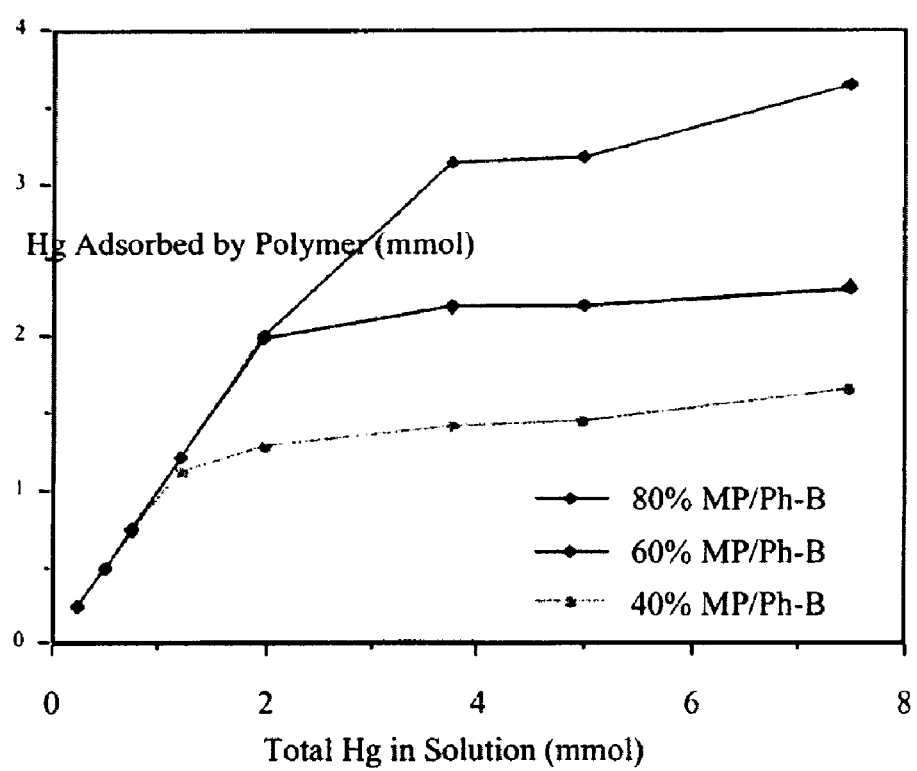
Figure 3: Mercury (II) uptake for MP/Ph-B xerogels.

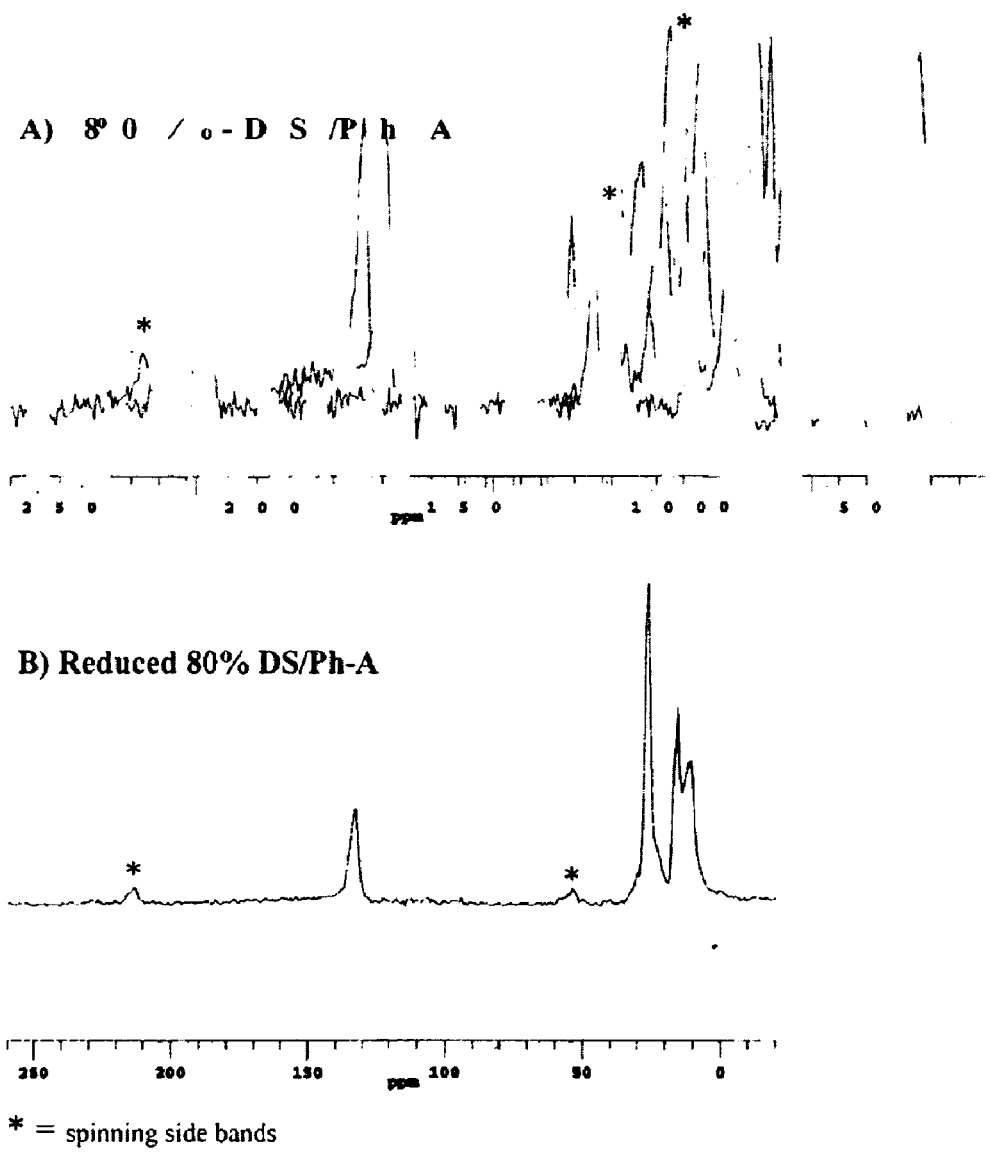
Figure 4: $^{13}$C CP MAS NMR of 80% dipropylenedisulfide/phenylene-bridged polysilsesquioxane A) before and B) after reduction.

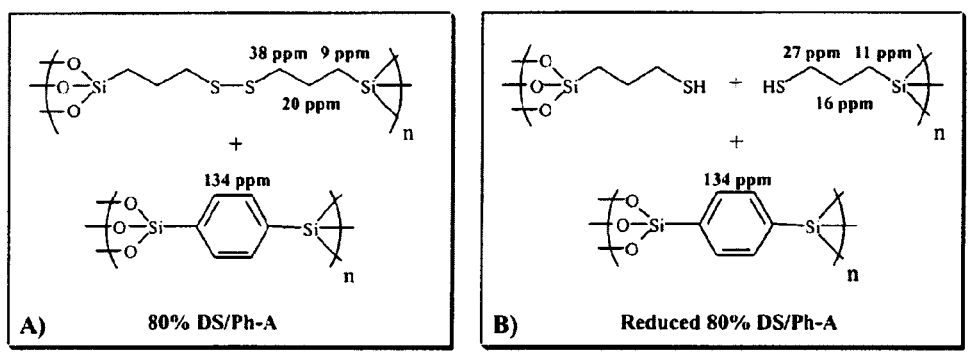
Figure 5: $^{13}$C CP MAS NMR shifts for base catalyzed 80% dipropylenedisulfide/phenylene-bridged xerogels A) before and B) after reduction.

HYBRID ORGANIC-INORGANIC ADSORBENTS

This application claims the benefit of U.S. Provisional Application Ser. No. 60/280,711, filed Mar. 30, 2001. This is also a continuation-in-part of U.S. application Ser. No. 09/872,097, filed Jun. 1, 2001, which claims the benefit of U.S. Provisional Application Ser. No. 60/279,337, filed Jun. 2, 2000. All of the above applications are expressly incorporated herein by reference.

FIELD OF THE INVENTION

The present invention relates generally to hybrid organic-inorganic adsorbents for decontamination of fluids, and more specifically, to dipropylenedisulfide-co-phenylene-bridged polysilsesquioxane compositions, methods of making dipropylenedisulfide-co-phenylene-bridged polysilsesquioxanes, and methods of use of dipropylenedisulfide-co-phenylene-bridged polysilsesquioxanes.

BACKGROUND OF THE INVENTION

The removal of atmospheric contaminants in industrial, commercial, or residential environments is a problem that is becoming more serious each year. Environmental control agencies are implementing increasingly stringent regulations to control emissions, and it is hence becoming more important to comply with environmental emissions standards. Current processes for the removal of atmospheric contaminants include incineration, adsorption, impingement, electrostatic attraction, centrifugation, sonic agglomeration, and ozonization.

Soil contamination is another environmental problem that is of great concern today. In particular, the removal of contaminants such as organic compounds and heavy metals from the soil is the focus of much research. The contamination of groundwater and, ultimately, drinking water is the driving force behind the extensive research being conducted in order to remove toxic and hazardous contaminants from the soil.

Numerous techniques for the decontamination of soil are disclosed in the art. One approach involves the excavation of soil followed by treating the soil with additives and chemicals to remove the contaminant. Another method involves the addition of additives or chemicals directly into the soil in order to convert the contaminant into a non-leachable form. The contaminant is rendered nonhazardous, and is not removed from the soil. Still another method to treat excavated soil is in situ soil remediation. This process involves contacting the soil with an aqueous extraction solution, directing the extractant solution through the soil so that the extractant solution interacts with the contaminant, and collecting the extractant solution containing the contaminant.

Another serious environmental concern is contamination occurring in aqueous-based solutions. In particular, disposing of wastewater is not only very expensive and time consuming, but also extremely harmful to the environment. Some areas of concern in the disposal of wastewater include negatively charged metals such as arsenic, molybdenum, and chromium; positively charged heavy metals such as copper, cadmium, nickel, lead, and zinc; and contaminants such as ammonia, mercury, arsenic and iron which react with oxygen.

Chemical procedures have attempted to cause a predetermined reaction between chemical additives and impurities contained within the waste stream. The most common reactions are designed to cause the impurities and the chemical additives to coagulate, wherein the particles increase in size and then separate by either floating on or settling below the treated water.

Physical procedures are designed to achieve similar results as chemical additive procedures, but to a lesser degree of purity in the final aqueous solution. Filters and centrifuges are the most common physical procedures employed to remove contaminants from aqueous solutions.

More cost-effective and efficient materials and methods are needed to remove contaminants from the air, water, and soil. The present invention discloses such materials and methods.

SUMMARY OF THE INVENTION

Hybrid organic-inorganic materials have been synthesized with potential applications for environmental and industrial processes. Most recently, hybrid mesoporous materials with functionalized monolayers containing thiol groups have been used as adsorbents to remove heavy metals from waste streams by Feng et al. 1997, Liu et al. 1998a, Mercier et al. 1998, and Liu et al. 1998b. See Feng et al., *Science* 276: 923–6 (1997), Liu et al., *Chemical Engineering and Technology* 21: 97–100 (1998); Mercier and Pinnavaia, *Environmental Science and Technology* 32: 2749–54 (1998); Liu et al., *Advanced Materials* 10: 161+ (1998), which are expressly incorporated herein by reference in their entirety. These functionalized hybrid materials show selectivity and high capacity for mercury (II) ions. These new materials also show potential for removing many other heavy metal pollutants.

The preparation of the heavy metal adsorbents entails the synthesis of highly ordered mesoporous silicate materials which are made by using surfactant micellar structures as templates, and functionalization of the resulting pore framework with suitable ligands. See Beck et al., *Journal of the American Chemical Society* 114: 10834–43 (1992); Kresge et al., *Nature* 359: 710–2 (1992); Raman et al., *Chemistry of Materials* 8: 1682–1701 (1996), which are expressly incorporated herein by reference in their entirety. These materials are known to have high surface areas and narrow pore distributions. It is hypothesized by Mercier and Pinnavaia that the highly regular pore structure of these materials offers controlled access to the channels as compared to other silicate materials with similar surface areas but broader pore distributions. See Mercier and Pinnavaia, *Advanced Materials*, 9: 500+(1997), expressly incorporated herein by reference in its entirety. Functionalization of these materials is achieved by reaction with 3-mercaptopropyltrialkoyxsilane. The thiol functional group is known to have high affinity for binding heavy metals, particularly mercury (11) ions. In order to allow functionalization of the pore framework with the trialkoxysilane, the pore surface must be rehydrated to replenish silanol groups that have been lost during thermal treatment. The rehydrated mesostructure is then allowed to react with 3-mercaptopropyltrimethoxysilane, resulting in covalent grafting of thiol moieties to the silanol groups lining the framework pore walls. See Mercier and Pinnovaia (1997).

Although the highly ordered mesoporous silicate materials show great potential as heavy metal adsorbents, the requirements of high ordering, mesoporosity, and high surface areas make the synthesis of these materials quite complex. In addition, the ligand loading capacity of these materials is limited by the quantity and availability of anchoring residual silanol groups on the pore surface. To that end, we have prepared functionalized hybrid inorganic-organic materials that are heavy metal adsorbents which have high ligand loading, do not require highly ordered structures yet possess high surface areas. These materials are made by copolymerization of 1,4-bis(triethoxysilyl)benzene and 3-mercaptopropyltriethoxysilane.

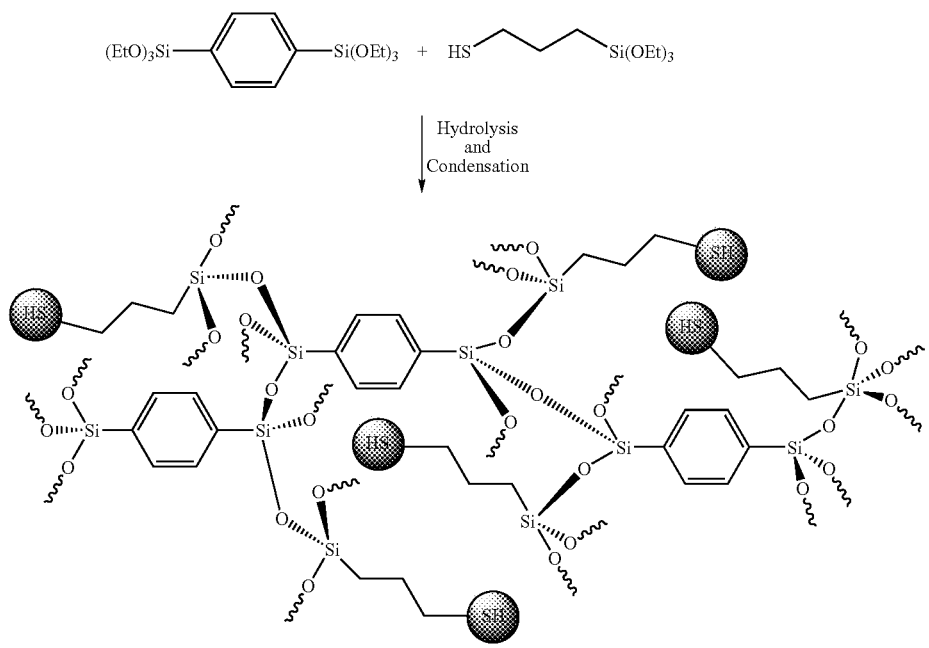

This novel hybrid polymer allows the incorporation of the functional thiol ligand within the pore structure, as well as on the surface of the material. The ligand loadings that are achieved with this method can be varied and is expected to be as high as 5.8 mmole of ligand per gram of adsorbent. This loading capacity is a significant improvement over the loading capacity of current state of the art functionalized silicate materials (1.5–3.0 mmol of Hg/g of adsorbent). See Feng et al. (1997); Liu et al. (1998); Mercier and Pinnavaia (1998); Liu et al. (1998b); and Mercier and Pinnavaia (1997). Furthermore, the synthesis of thiol functionalized phenylene-bridged polysilsesquioxanes is straightforward in comparison to the multi-step synthesis of the functionalized mesoporous materials.

The present invention also discloses hybrid materials that incorporate a disulfide bridge in the framework. The disulfide group can serve as protected thiol groups. The disulfide moiety is incorporated into the silicate matrix by homopolymerization of bis(3-triethoxysilylpropyl)disulfide or by copolymerization with 1,4-bis(triethoxysilyl)benzene, thus creating a porous network.

Scheme 1:
Preparation of dipropylenedisulfide and dipropylenedisulfide-co-phenylene-bridged polysilsesquioxane.

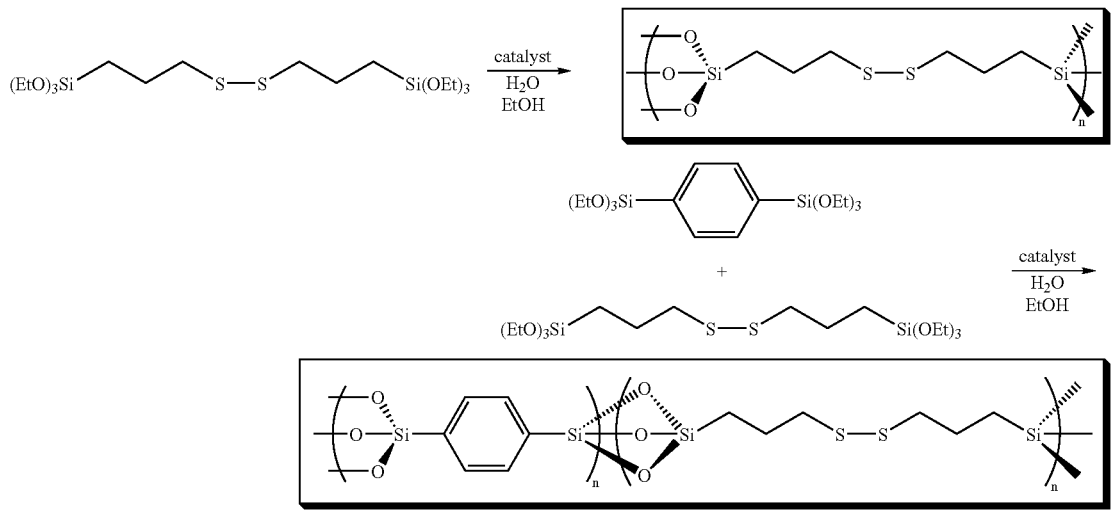

In the resulting materials, the disulfide bridge behaves as a surrogate for the thiol functional group. Reduction of the disulfide bridge can provide functional thiol groups without compromising the integrity of the silicate matrix. The reduction and oxidation cycle of the disulfide moiety may also provide a method for modulating the physical properties of the material, such as surface area and pore size distribution.

Post-polymerization modification of the disulfide materials can produce heavy metal adsorbents with substantially higher ligand loading capacities (theoretical loading ~7.8 mmol of Hg/g of adsorbent based on 1:1 ratio of thiol ligand to metal assuming complete reduction) than any material that has been previously reported.

BRIEF DESCRIPTION OF THE DRAWINGS

FIG. 1: Interconversion of disulfide and thiol functionality.

FIG. 2: $^{13}C$ NMR of bis(3-triethoxysilylpropyl)disulfide using bromine as the oxidant.

FIG. 3: Mercury (II) uptake for MP/Ph-B xerogels.

FIG. 4: $^{13}C$ CP MAS NMR of 80% dipropylenedisulfide/phenylene-bridged polysilsequioxane A) before and B) after reduction.

FIG. 5: 13C CP MAS NMR shifts for base catalyzed 80% dipropylenedisulfide/phenylene-bridged xerogels A) before and B) after reduction.

DETAILED DESCRIPTION

The monomer was isolated by high vacuum distillation in yields ranging from 43–47% (literature 55%).

Two different routes were used for the synthesis of bis(3-triethoxysilylpropyl)disulfide (DS-0). See Buder, *Anorg. Chem. Org. Chem,* 34B: 790–3 (1979); and Wu et al. *Synthetic Communications* 26: 191–6 (1996), which are both expressly incorporated herein by reference in their entirety. Both methods involved oxidative coupling of commercially available 3-mercaptopropyltriethoxysilane.

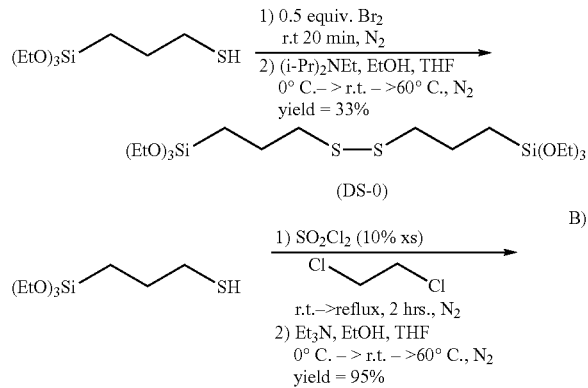

-continued

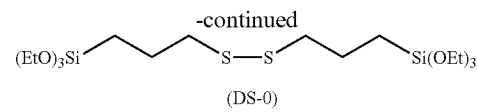

(DS-0)

Oxidation of the thiol with bromine (route A) gave the symmetrical disulfide. No solvent was used. In this reaction bromine acts as both the oxidizing reagent and indicator. The reaction has been reported by Wu et al. to give essentially quantitative yields for simple alkyl thiols. See Wu et al., *Synthetic Communications* 26: 191–6 (1996). However, the reaction of 3-mercaptopropyltriethoxysilane with bromine may be complicated by reaction of the triethoxysilyl groups with HBr, a by-product of the reaction.

Scheme 4:
Reaction of bis(3-triethoxysilyl)propyl disulfide with HBr.

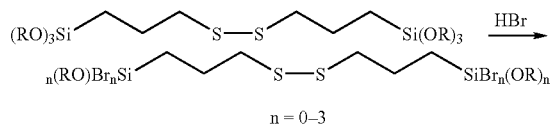

n = 0–3

The product from bromine coupling may be contaminated with mixtures of bromo- and alkoxy-silanes. This contamination may be remedied by treating the reaction mixture with ethanol and diisopropylethylamine. The isolated product gave the expected $^1H$ NMR shifts but close inspection of the $^{13}C$ NMR showed additional peaks that overlapped or were shifted slightly from the desired product peaks (FIG. 2).

A possible explanation may involve further reaction of the newly formed disulfide with residual bromine. This seems very possible since the product still retained some of the bromine color (clear light brown solution).

Synthesis of pure disulfide monomer was achieved by oxidation of the 3-mercaptopropyltriethoxysilane with sulfuryl chloride (route B). This reaction was reported by Buder (1979) to give essentially quantitative yield with similar alkyl thiols and purification required only removal of the solvent and by-products ($SO_2$, and HCl) in vacuo. See Buder, *Anorg. Chem. Org. Chem.* 34B: 790–3 (1979). The removal of the HCl gas, which was produced during the reaction, was facilitated by rigorously bubbling nitrogen gas through the refluxing reaction mixture. After removal of solvent and by-products, the clear solution was slightly tinted yellow. The clear yellow solution was then passed through a plug of neutral alumina yielding a colorless liquid. The $^1H$ NMR of the recovered product gave the expected chemical shifts for the symmetrical disulfide. $^{13}C$ NMR showed extraneous peaks which overlapped or exhibited very similar chemical shifts to the desired product peaks. In order to remedy this problem, the reaction conditions were altered slightly by addition of an ethanolysis step (trialkylamine and ethanol). This converted the chlorosilane group to the desired triethoxysilyl unit. Optimization and refinement of the reaction conditions allowed for the preparation of pure monomer (>97% as determined by GC) in excellent yields (95%).

Compounds of the Present Invention

The present invention discloses a compound having a formula of:

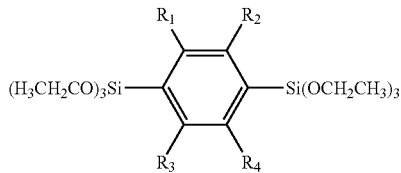

or a derivative or analog thereof, wherein:

$R_1$–$R_4$ are independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$, cycloalkyl, $C_5$–$C_7$ cycloalkenyl, benzyl, phenyl, halides, ethers, alcohols, sulfides, amines, nitro, nitrile, azide, and a heterocycle; and wherein the halides comprise flourine, chlorine, bromine, and iodine; and wherein the heterocycle is selected from the group consisting of 2-pyridyl, 3-pyridyl, 4-pyridyl, furan, and thiophene; and wherein the ethers are of the general formula —O—$R_5$, wherein $R_5$ is independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, and a heterocycle; and wherein the heterocycle is selected from the group consisting of 2-pyridyl, 3-pyridyl, 4-pyridyl, furan, and thiophene; and wherein the amines are of the general formula —N(—$R_6$)—$R_7$, wherein $R_6$ and $R_7$ are independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, and a heterocycle; and wherein the heterocycle is selected from the group consisting of 2-pyridyl, 3-pyridyl, 4-pyridyl, furan, and thiophene.

The present invention further discloses a compound of formula

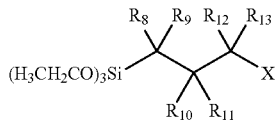

or a derivative or analog thereof, wherein:

$R_8$–$R_{13}$ are independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, halides, ethers, alcohols, sulfides, amines, nitro, nitrile, azide, and a heterocycle; and wherein X is independently selected from the group consisting sulfur, oxygen, nitrogen, phosphorus, selenium, and boron; and wherein the halides comprise flourine, chlorine, bromine, and iodine; and wherein the heterocycle is selected from the group consisting of 2-pyridyl, 3-pyridyl, 4-pyridyl, furan, and thiophene; and wherein the ethers are of the general formula —O—$R_{14}$ wherein $R_{14}$ is independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, and a heterocycle; and wherein the heterocycle is selected from the group consisting of 2-pyridyl, 3-pyridyl, 4-pyridyl, furan, and thiophene; and wherein the amines are of the general formula —N(—$R_{15}$)—$R_{16}$, wherein $R_{15}$ and $R_{16}$ are independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, and a heterocycle; and wherein the heterocycle is selected from the group consisting of 2-pyridyl, 3-pyridyl, 4-pyridyl, furan, and thiophene.

The present invention still further discloses a compound of formula:

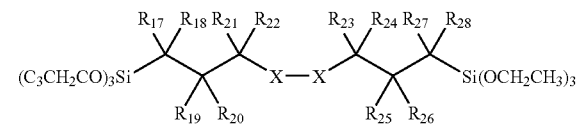

or a derivative or analog thereof, wherein:

R17–R28 are independently selected from the group consisting of hydrogen, C1–Cn straight or branched chain alkyl, C1–Cn straight or branched chain alkenyl, wherein n is greater than one; aryl, C3–C8 cycloalkyl, C5–C7 cycloalkenyl, benzyl, phenyl, halides, ethers, alcohols, sulfides, amines, nitro, nitrile, azide, and a heterocycle; and wherein X is selected from the group consisting of sulfur, oxygen, nitrogen, phosphorus, selenium, and boron, or wherein X—X is selected from the group consisting of anhydrides, or phosphorus anhydrides; and wherein the halides comprise flourine, chlorine, bromine, and iodine; and wherein the heterocycle is selected from the group consisting of 2-pyridyl, 3-pyridyl, 4-pyridyl, furan, and thiophene; and wherein the ethers are of the general formula —O—R29 wherein R29 is independently selected from the group consisting of hydrogen, C1–Cn straight or branched chain alkyl, C1–Cn straight or branched chain alkenyl, wherein n is greater than one; aryl, C3–C8 cycloalkyl, C5–C7 cycloalkenyl, benzyl, phenyl, and a heterocycle; and wherein the heterocycle is selected from the group consisting of 2-pyridyl, 3-pyridyl, 4-pyridyl, furan, and thiophene; and wherein the amines are of the general formula —N(—$R_{30}$)—$R_{31}$, wherein $R_3$ and $R_{31}$ are independently selected from the group consisting of hydrogen, $C_1$–$C_n$ straight or branched chain alkyl, $C_1$–$C_1$ straight or branched chain alkenyl, wherein n is greater than one; aryl, $C_3$–$C_8$ cycloalkyl, $C_5$–$C_7$ cycloalkenyl, benzyl, phenyl, and a heterocycle; and wherein the heterocycle is selected from the group consisting of 2-pyridyl, 3-pyridyl, 4-pyridyl, furan, and thiophene.

The present invention further discloses a compound of 1,4-bistriethoxysilylbenzene and bis-(3-triethoxysilylpropyl)disulfide having a formula

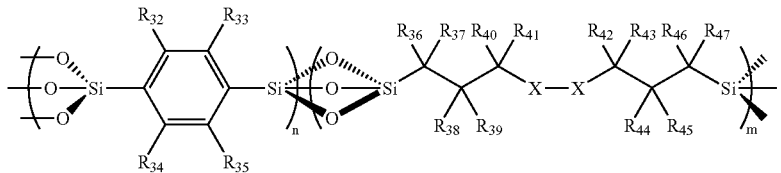

or a derivative or analog thereof wherein:
n is zero or larger; and
m is zero or larger; and
$R_{32}$–$R_{35}$ are independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, halides, ethers, alcohols, sulfides, amines, nitro, nitrile, azide, and a heterocycle; and $R_{36}$–$R_{47}$ are independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, halides, ethers, alcohols, sulfides, amines, nitro, nitrile, azide, and a heterocycle; and wherein X is selected from the group consisting of sulfur, oxygen, nitrogen, phosphorus, selenium, and boron, or wherein X—X is selected from the group consisting of anhydrides, or phosphorus anhydrides; and wherein the halides comprise flourine, chlorine, bromine, and iodine; and wherein the heterocycle is selected from the group consisting of 2-pyridyl, 3-pyridyl, 4-pyridyl, furan, and thiophene; and wherein the ethers are of the general formula —O—$R_{48}$ wherein $R_{48}$ is independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, and a heterocycle; and wherein the heterocycle is selected from the group consisting of 2-pyridyl, 3-pyridyl, 4-pyridyl, furan, and thiophene; and wherein the amines are of the general formula —N(—$R_{49}$)—$R_{50}$, wherein $R_{49}$ and $R_{50}$ are independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, and a heterocycle; and wherein the heterocycle is selected from the group consisting of 2-pyridyl, 3-pyridyl, 4-pyridyl, furan, and thiophene.

A compound of 1,4-bistriethoxysilylbenzene and mercaptopropyltriethoxysilane

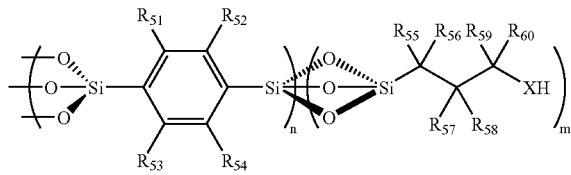

or a derivative or analog thereof:
wherein n is zero or larger; and
wherein m is zero or larger; and
wherein $R_{51}$–$R_{54}$ are independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, halides, ethers, alcohols, sulfides, amines, nitro, nitrile, azide, and a heterocycle; and wherein $R_{55}$–$R_{60}$ are independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, halides, ethers, alcohols, sulfides, amines, nitro, nitrile, azide, and a heterocycle; and wherein X is selected from the group consisting of hydrogen, sulfur, oxygen, nitrogen, phosphorus, selenium, and boron; and wherein the halides comprise flourine, chlorine, bromine, and iodine; and wherein the heterocycle is selected from the group consisting of 2-pyridyl, 3-pyridyl, 4-pyridyl, furan, and thiophene; and wherein the ethers are of the general formula —O—$R_{61}$, wherein $R_{61}$ is independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, and a heterocycle; and wherein the heterocycle is selected from the group consisting of 2-pyridyl, 3-pyridyl, 4-pyridly, furan, and thiophene; and wherein the amines are of the general formula —N(—$R_{62}$)—$R_{63}$, wherein $R_{62}$ and $R_{63}$ are independently selected from the group consisting of hydrogen, $C_1$–$C_n$ straight or branched chain alkyl, $C_1$–$C_n$ straight or branched chain alkenyl, wherein n is greater than one; aryl, $C_3$–$C_8$ cycloalkyl, $C_5$–$C_7$ cycloalkenyl, benzyl, phenyl, and a heterocycle; and wherein the heterocycle is selected from the group consisting of 2-pyridyl, 3-pyridyl, 4-pyridyl, furan, and thiophene.

Synthesis of Sol-Gel Materials

New sol-gel materials containing 3-mercaptopropyltriethoxysilane and 1,4-bis(triethoxysilyl)benzene were prepared under both acid and base catalyzed conditions. The gels were hydrolitically condensed using 0.4M monomer solutions in ethanol, 6:1 mole ratio of water to monomer, and 10.8 mol % of catalyst (1N HCl or 1N NaOH). Polymerizations were carried out at room temperature in capped polyethylene bottles. Polymers are denoted by monomer (MP=3-mercaptopropyltriethoxysilane and Ph=1,4-bis(triethoxysilyl)benzene, DS=bis(3-triethoxysilylpropyl)disulfide) followed by the type of catalyst used in the gel's preparation ('A' for acid and 'B' for base). After gelation, the gels were aged for twice the gelation time (approx. one week) by allowing to stand at room temperature. The crushed gels were soaked in water overnight and filtered to remove water and air-dried for 2 days. The clear xerogels were ground into fine white powders and dried under vacuum.

Scheme 5:
Mercaptopropylene doped/phenylene polysilsesquioxane.

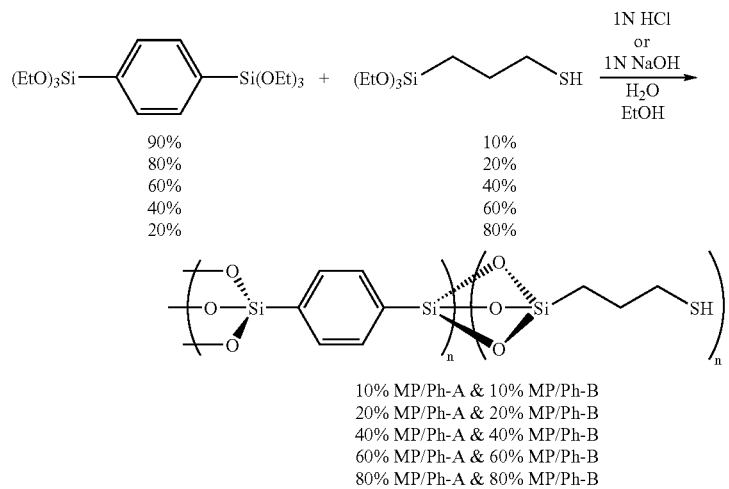

10% MP/Ph-A & 10% MP/Ph-B
20% MP/Ph-A & 20% MP/Ph-B
40% MP/Ph-A & 40% MP/Ph-B
60% MP/Ph-A & 60% MP/Ph-B
80% MP/Ph-A & 80% MP/Ph-B

*percentages represent mole percent of each monomer
MP = mercaptopropyltriethoxysilane, Ph = 1,4-Bis(triethoxysilyl)benzene
A = acid catalyzed, B = base catalyzed In general, the base catalyzed materials gelled within several hours to several days even at high 3-mercaptopropyltriethoxysilane loadings. In contrast, the acid catalyzed gels were slow to react and gelation times took several days to months.

TABLE 1

Gelation times for various MP/Ph materials.

| Mercaptopropylene/<br>Phenylene Xerogels | Gelation times |
|---|---|
| 100% PH-A | 2 days |
| 10% MP/Ph-A | 5 days |
| 20% MP/Ph-A | 7 days |
| 40% MP/Ph-A | 1 month |
| 60% MP/Ph-A | ~6 months |
| 80% MP/Ph-A | no gel |
| 100% PH-B | 2 hrs |

TABLE 1-continued

Gelation times for various MP/Ph materials.

| Mercaptopropylene/<br>Phenylene Xerogels | Gelation times |
|---|---|
| 10% MP/Ph-B | 2 hrs |
| 20% MP/Ph-B | 2 hrs |
| 40% MP/Ph-B | 2 hrs |
| 60% MP/Ph-B | 2 hrs |
| 80% MP/Ph-B | 2 days |

A series of dipropylenedisulfide/phenylene-bridged sol-gel materials were made from hydrolytic condensation of bis(triethoxysilylpropyl)disulfide and 1,4-bis(triethoxysilyl)benzene under both acid and base catalyzed conditions using the same polymerization and processing conditions as that of mercaptopropylene/phenylene-bridged materials (MP/Ph) materials.

Scheme 6:
Dipropylenedisulfide and dipropylenedisulfide/phenylene-bridged polysilsequioxanes.

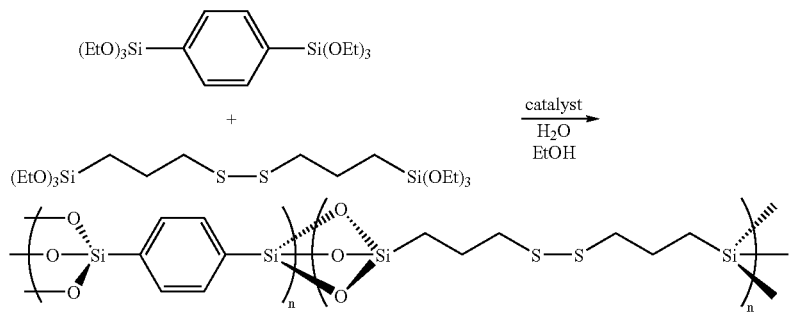

20% DS/Ph-A & 20% DS/Ph-B
40% DS/Ph-A & 40% DS/Ph-B
60% DS/Ph-A & 60% DS/Ph-B
80% DS/Ph-A & 80% DS/Ph-B
100% DS-A & 100% DS-B

The gelation times for these materials parallel that of the mercaptopropylene/phenylene-bridged xerogels (MP/Ph). Notably, gelation times for the base catalyzed materials (DS/Ph-B) were much faster than that of the acid catalyzed materials (DS/Ph-A). However, in contrast to MP/Ph-A materials, all acid catalyzed dipropylenedisulfide/phenylene-bridged materials formed gels with the exception of 10% DS-A.

TABLE 2

Gelation times for DS/Ph materials.

| Dipropylenedisulfide/Phenylene Xerogel | Gelation times |
|---|---|
| 20% DS/Ph-A | 2 days |
| 40% DS/Ph-A | 2 days |
| 60% DS/Ph-A | 3 days |
| 80% DS/Ph-A | 3 days |
| 100% DS-A | precipitated |
| 20% DS/Ph-B | 1 hr |
| 40% DS/Ph-B | 1 hr |
| 60% DS/Ph-B | 1 hr |
| 80% DS/Ph-B | 1 hr |
| 100% DS-B | 1 hr |

Surface Area and Porosity

Nitrogen adsorption porosimetry analyses of mercaptopropyl/phenlyene-bridged materials showed a distinct difference between the acid and base catalyzed xerogels. All acid catalyzed mercaptopropylene/phenlyene-bridged materials, 20%, 40%, 60% MP/Ph-A (80% MP/Ph-A did not gel), had low surface areas (SA<100 $m^2/g$). In contrast, the base catalyzed mercaptopropyl/phenylene-bridged xerogels exhibited high surface areas and gave characteristic type IV nitrogen adsorption isotherms which are indicative of a porous adsorbent possessing pores in both micropore to mesopore regions.

TABLE 3

Surface area and porosity of base catalyzed mercaptopropylene/phenylene-bridged polysilsesquioxane.

| Base Catalyzed Materials | Surface Area ($m^2/g$) | Avg. Pore Diameter (Å) | Total Pore Vol. (cc/g) |
|---|---|---|---|
| 100% Ph-B | 1045 | 30 | 0.79 |
| 20% MP/Ph-B | 928 | 32 | 0.73 |
| 40% MP/Ph-B | 848 | 36 | 0.73 |
| 60% MP/Ph-B | 707 | 51 | 0.91 |
| 80% MP/Ph-B | 449 | 96 | 1.08 |

In contrast to the acid catalyzed materials, the base catalyzed mercaptopropylene/phenylene-bridged polysilsesquioxanes (MP/Ph-B) displayed high surface areas and porosity. The analysis of the base catalyzed series showed that sol-gel materials could be made with high ligand loadings without sacrificing surface areas and porosity. Especially noteworthy is that even at 80% thiol loading, a mesoporous sol-gel material formed in one day. It should be noted that pure mercaptopropyltriethoxysilane does not form a gel under these conditions but would provide a viscous T-resin. Therefore, an important role can be attributed to the phenylene-bridging moiety in contributing to the materials bulk properties.

A trend was observed in the base catalyzed series. A decrease in surface area was observed with increasing thiol loading. With the decrease in surface area, there was concomitant increase in pore diameter. This trend is similar to that observed by Oviatt et al. (1993) in base catalyzed alkylene-bridged polysilsesquioxanes. See Oviatt et al., *Chemistry of Materials* 5: 943–50 (1993), which is expressly incorporated herein by reference in its entirety. As in the alkylene series, a possible explanation for the increase in pore diameter of MP/Ph-B materials can be attributed to increasing density of hydrocarbon spacer units which may induce microphase separation or aggregation of the alkyl spacers from the silicate moieties. This microphase separation may lead formation of void spaces between the organic and inorganic components resulting in an increase in mean pore diameter. The trend of decreasing surface area may result from decreased crosslinking with higher ligand loading which in turn can cause collapse of the pore network during polymerization and/or processing.

Nitrogen porosimetry analyses of dipropylenedisulfide/phenylene-bridged materials (DS/Ph) resulted in a trend similar to that of the mercaptopropylene/phenylene-bridged materials. All acid catalyzed xerogels were non-porous with the exception of 20% DS/Ph-A (332 $m^2/g$, 23Å, 0.19 cc/g). Whereas, all base catalyzed xerogels (DS/Ph-B) exhibited high surface areas and gave characteristic type IV nitrogen adsorption isotherms with pore diameters in the mesopore region. The total pore volume of the disulfide bridged materials were lower than those of the MP/Ph-B materials (approximately ½).

TABLE 4

Surface area and porosity of base catalyzed dipropylenedisulfide/phenylene-bridged xerogels.

| Base Catalyzed Materials | Surface Area ($m^2/g$) | Avg. Pore Diameter (Å) | Total Pore Vol. (cc/g) |
|---|---|---|---|
| 20% DS/Ph-B | 613 | 23 | 0.36 |
| 40% DS/Ph-B | 500 | 25 | 0.31 |
| 60% DS/Ph-B | 374 | 29 | 0.27 |
| 80% DS/Ph-B | 113 | 171 | 0.49 |
| 100% DS-B | 58 | 201 | 0.29 |

As with the base catalyzed mercaptopropylene/phenylene-bridged (MP/Ph-B) series, base catalyzed dipropylene/phenylene-bridged xerogels (DS/Ph-B) revealed a trend of decreasing surface area with increasing ligand loading. The decrease in surface area was also accompanied by an increase in average pore diameter. The trend of decreasing surface area may be attributed to higher loadings of the more flexible disulfide bridge which in turn can cause collapse of the pore network during polymerization or processing. As observed in the base catalyzed mercaptopropylene/phenylene-bridged systems (MP/Ph-B), the increase in pore diameter may be attributed to increasing density of hydrocarbon spacer units which may induce microphase separation or aggregation of the alkyl spacers from the silicate units. This microphase separation may lead to formation of void spaces between the organic and inorganic components resulting in an increase in mean pore diameter.

Hg$^{+2}$ Uptake Studies for Mercaptopropylene/Phenylene Xerogels

Mercury adsorption studies were conducted on the mercaptopropylene/phenylene materials. Mercury(II) nitrate in water was used as the Hg$^{+2}$ source. The experiment consisted of taking 10 mg portions of the doped materials and stirring for 18–24 hours at room temperature with 50 mL volumes of Hg(NO$_3$)$_2$ solutions at initial concentrations that ranged from 0–300 ppm. Mercury(II) concentrations were determined before and after treatment by colormetric analysis using diphenylthiocarbazone as an indicator. See Marezenko, *Separation and spectrophotometric determination of elements*; (2$^{nd}$ ed, Halsted Press: Chichester West Sussex, N.Y.) (1986), which is incorporated herein by reference in its entirety. The diphenylthiocarbazone method is accurate for determination of mercury (II) as low as 1 ppm. Calibration for the colormetric analysis was preformed using Hg(NO$_3$)$_2$ standards that ranged from 0–300 ppm. Mercury uptake studies were conducted with base catalyzed MP/Ph-B materials since they exhibited high surface areas and porosities, which we believed would be optimal for accessibility of the metal with the thiol ligand. The results are summarized below.

TABLE 5

Hg$^{+2}$ adsorption for mercaptopropylene/phenylene xerogels.

| Base Catalyzed Materials | Hg + 2 Adsorbed (mmol/g) | Theoretical Max. Adsorption (mmol/g) |
|---|---|---|
| 100% Ph-B | — | 0 |
| 20% MP/Ph-B | 2.34 | 1.18 |
| 40% MP/Ph-B | 1.66 | 2.51 |
| 60% MP/Ph-B | 2.32 | 4.04 |
| 80% MP/Ph-B | 3.26 | 5.8 |

MP/Ph-B materials adsorbed significant quantities of mercury (II). For the Hg$^{+2}$ uptake experiments, pure phenyl-bridged polysilsesquioxane (100% Ph-B) was used as the control. Absorption of Hg$^{+2}$ by 100% Ph-B was negligible. It can be concluded that the mercaptopropyl ligand is solely responsible for the uptake of Hg$^{+2}$. The maximum Hg$^{+2}$ uptake for MP/Ph-B materials was determined at the saturation point where mercury (II) uptake of the material leveled off and no further adsorption was observed.

As seen in Table 5, the maximum uptake of Hg$^{+2}$ in the MP/Ph-B materials were lower than the theoretical capacity maximum which was based upon the mole ratios of thiol ligand assuming one to one association with mercury (II) ions. This indicated that not all thiol ligand sites were accessible to mercury (II) or that the stoichiometry is not 1:1. One possible explanation for adsorption less than the theoretical maximum may be attributed to irregular pore shapes which can become blocked during Hg$^{+2}$ uptake experiments. Additionally, potential swelling of the material during heavy metal uptake may restrict pore channels and limit access to the thiol ligand. It was also observed that the Hg$^{+2}$ uptake tended to deviate more from the theoretical maximum with increased ligand loading. For example, 40% MP/Ph-B adsorbed 66% of the theoretical capacity, whereas, 80% MP/Ph-B adsorbed only 57% of capacity. This trend may be correlated with the decrease in surface area with increasing ligand loading. Decreased surface areas and porosity would limit access of Hg$^{+2}$ ions to the thiol groups. Even though these materials adsorbed less than the theoretical capacity, their mercury(II) adsorption capacity are currently the highest that have been reported for any silicate material.

Acid catalyzed mercaptopropylene/phenylene materials (MP/Ph-A) were also tested for mercury(II) adsorption under identical conditions to MP/Ph-B materials, and they proved to be only slightly less effective for Hg$^{+2}$ uptake. For example, 60% MP/Ph-A adsorbed 2.1 mmol of Hg$^{+2}$/g of material or 52% of the theoretical adsorption capacity. The comparable base catalyzed material (60% MP/Ph-A) adsorbed 2.3 mmol of Hg$^{+2}$/g of material or 57% of the theoretical adsorption capacity. The similarity in adsorption capacity is quite remarkable considering that 60% MP/Ph-A was non-porous. This result is particularly surprising when one considers that 60% MP/Ph-A has a mercury(II) adsorption capacity that approaches that of thiol functionalized ordered mesoporous materials with surface areas approximately 1000 m$^2$/g. This demonstrates that the thiol loading capacities available to the polysilsesquioxanes are not dependent on high surface area.

Post-Polymerization Modification of Disulfide Bridged Materials

In principle, reduction of the disulfide bridge should generate two thiol groups, producing materials with theoretical capacities as high as 7.8 mmole per gram of adsorbent based on a 1:1 stoichiometry of Hg$^{+2}$ to thiol group. Post-polymerization modification of dipropylenedisulfide/phenylene-bridged materials (DS/Ph) was attempted to provide an even more efficient heavy metal adsorbent with substantially higher ligand loading capacities. There are numerous methods for reducing disulfides. The present invention employed trialkylphosphines as the reducing agent.

Scheme 7:
Reduction of dipropylenesulfide/phenylene-bridged polysilsequioxane.

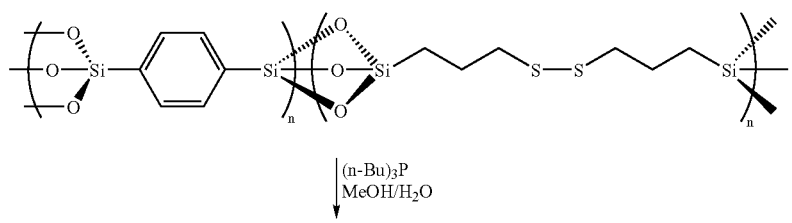

-continued

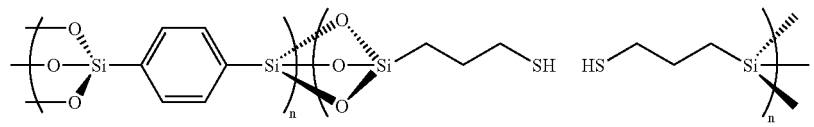

It has been previously reported by Humphrey and Potter (1965) and by Humphrey and Hawkins (1964), that reductions using tri-n-butylphosphine gives quantitative cleavage of similar dialkyl disulfides. See Humphrey and Potter, *Analytical Chemistry* 37: 164–5 (1965); and Humphrey and Hawkins, *Analytical Chemistry* 36: 1812–4 (1964), which are both expressly incorporated herein by reference in their entirety. The mild conditions associated with this reaction was thought to be more compatible with the silicate matrix. It was reasoned that reduction of the disulfide moiety could be accomplished effectively without altering the inorganic framework. Initial reduction studies were attempted on 80% DS/Ph-A. It was rationalized that if effective reduction of a non-porous material (80% DS/Ph-A) could be accomplished, then complete reduction of the more porous base catalyzed dipropylenesulfide/phenylene-bridged xerogels (DS/Ph-B) would be highly feasible.

The course of the reaction could be followed by solid state NMR. Consequently, reduction of the 80% DS/Ph-A was verified by comparison of solid state $^{13}$C CP MAS NMR before and after reduction.

The $^{13}$C CP MAS NMR of the native compound (80% DS/Ph-A) showed the propylene carbon resonances for the α, β, and γ carbons at $\delta_c$=9, 20, 38 and aryl carbon resonance at $\delta_c$=134. In contrast, the $^{13}$C MAS NMR of the reduced material (Red. 80% DS/Ph-A) showed the propylene carbon resonances for the α, β, and γ carbons at $\delta_c$=11, 16, 27 and the aryl carbon resonance at $\delta_c$=134.

Even though, the uncertainty in solid state $^{13}$C CP MAS NMR is approximately ±2 ppm, the chemical shift of the γ-carbon served as a useful diagnostic to indicate reduction of the disulfide bridge. The chemical shift difference for γ-carbons is approximately 10 ppm (38 ppm for disulfide material and 27 ppm for reduced disulfide material), which is a range that is readily discernable in solid state $^{13}$C CP MAS NMR. The observed resonances for the reduced 80% dipropylene/phenylene-bridged polysilsesquioxane is consistent with a mercaptopropyl-substituted polysilsesquioxane ($\delta_c$=9, 27). The $^{13}$C CP MAS NMR of the reduced material (Red. 80% DS/Ph-A) indicated quantitive reduction of the disulfide bridge, even though the material was non-porous.

$^{29}$Si SP MAS NMR was used to examine if any further sol-gel condensation had occurred under the reduction conditions. The $^{29}$Si resonances were observed for 80% DS/Ph-A at −60 ppm($T^2$) and −68 ppm ($T^3$). Deconvolution of the $^{29}$Si SP MAS NMR gave the percentage of $T^2$ (55.2%), and $T^3$ (44.8%) silicons. The calculated percentage of each T species was then used to determine the overall degree of condensation which was 82% for 80% DS/Ph-A. The reduced dipropylenedisulfide/phenylene-bridged xerogel (Red. 80% DS/Ph-A) provided similar $^{29}$Si resonances at −57 ppm($T^2$) and −66 ppm ($T^3$). Deconvolution of the $^{29}$Si SP MAS NMR gave the percentage of differing populations of $T^2$ (44.9%), and $T^3$ (55.1%) silicons resulting in a calculated degree of condensation of 85% for Red. 80% DS/Ph-A. The uncertainty (±5%) associated with calculation of the degree of condensation arises from deconvolution of the peak areas. Therefore, if one considers this uncertainty, two materials have very similar percentage of condensations with only slight increase in the degree of condensation observed. This suggest that there is little change in the inorganic silicate network resulting from the protocol for reductive cleavage of the disulfide linkage.

Surface Area and Porosity of Dipropylenedisulfide/Phenylene Xerogels

In order to establish if any change in the materials' surface area and porosity took place as a result of reduction of the disulfide linkage, 80% DS/Ph-A was analyzed before and after reduction using nitrogen adsorption porosimetry. The analysis revealed that both materials were non-porous. Reduction of dipropylenedisulfide/phenylene-bridged polysilsesquioxanes does not produce a measurable change in the porosity. Porosity and surface area are only a coarse measurement of morphology. In this case, even though the material has undergone substantial chemical cleavage, there is no indication that the process results in the creation of internal pore volume or surface area.

$Hg^{+2}$ Uptake of Dipropylenedisulfide/Phenylene Xerogels $Hg^{+2}$ adsorption studies were conducted on base catalyzed 80% dipropylenedisulfide/phenylene-bridged material (80% DS/Ph-A) before and after reduction of the disulfide linkage.

TABLE 6

$Hg^{+2}$ adsorption for 80% dipropylenedisulfide/phenylene-bridge polysilsesquioxane A) before and B) after reduction.

| Acid Catalyzed Materials | Hg + 2 Adsorbed (mmol/g) | Theoretical Max. (mmol/g) |
|---|---|---|
| A) 80% DS/Ph-A | 0.00 | 0 |
| B) Red. 80% DS/Ph-A | 0.00 | 6.67 |

The 80% dipropylenedisulfide/phenylene-bridged material (80% DS/Ph-A) did not adsorbed any $Hg^{+2}$ ions. Surprisingly, reduction of 80% DS/Ph-A did not provide an increase in $Hg^{+2}$ uptake for the newly modified material as expected. This result would seem to indicate that there are no available thiol ligands for adsorption of mercury (II) ions. However, presence of thiol groups in the Red. 80% DS/Ph-A xerogel has been previously verified by solid state NMR. Therefore, one explanation may involve further collapse of the pore network after elimination of the disulfide linkage. Consequently, the collapse of the pore structure can prohibit access of the metal to the ligand.

Scheme 8:
Potential collapse of the silicate network after reduction of the disulfide linkage.

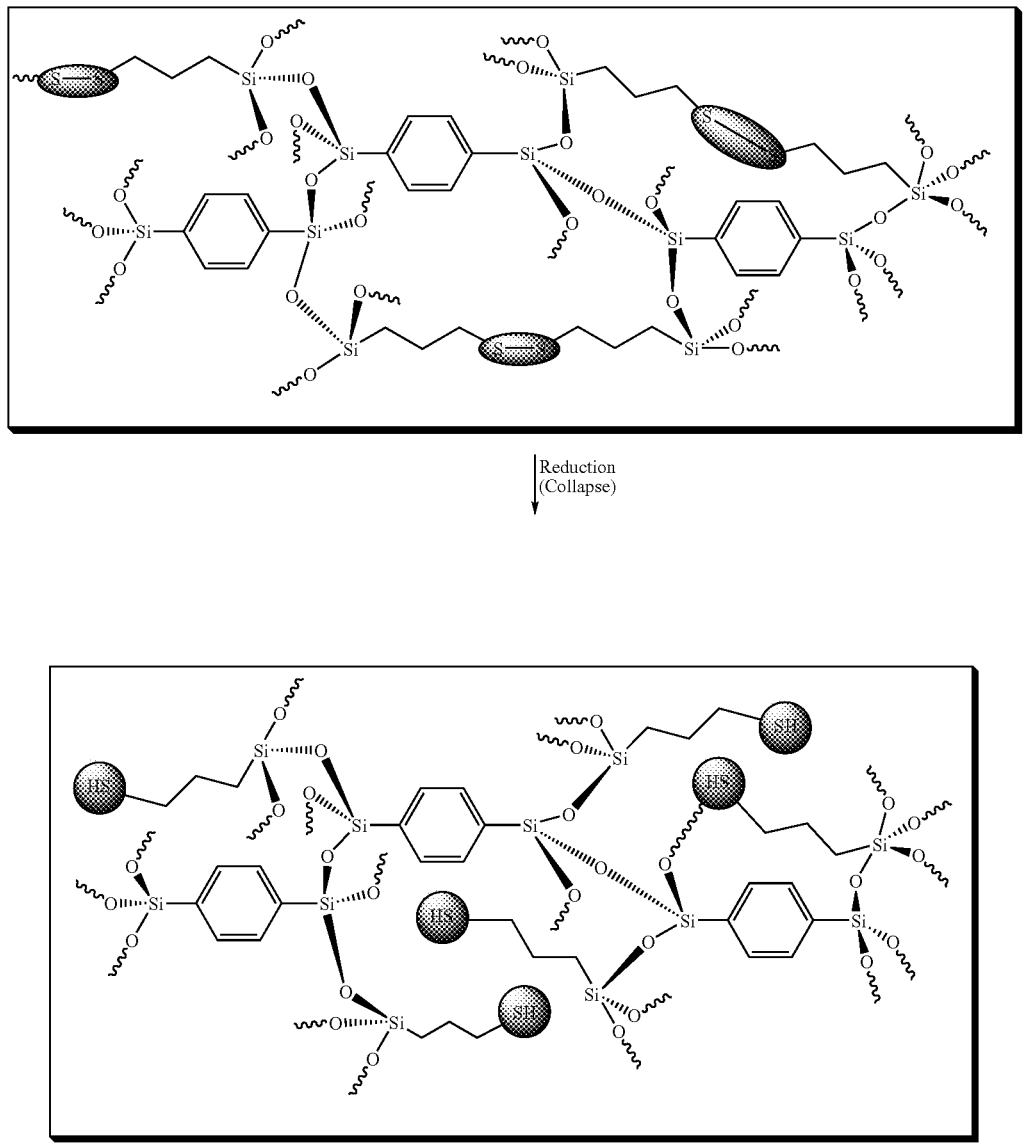

From the observations above, reductions were studied on materials with lower ligand loading and higher content of phenylene-bridging units, reasoning that increased incorporation of the rigid phenylene-bridging units would provide stability in the pore network to withstand collapse of the pore structure under these reduction conditions. Thus, reduction of 30% dipropylenedisulfide/phenylene-bridged polysilsesquioxane (30% DS/Ph-A) was attempted using tri-n-butylphosphine. The reduced 30% DS/Ph-A showed significant increase in uptake compared to the unreduced form.

TABLE 7

$Hg^{+2}$ adsorption for 30% dipropylenedisulfide/phenylene-bridge polysilsesquioxane A) before and B) after reduction.

| Acid Catalyzed Materials | Hg +2 Adsorbed (mmol/g) | Theoretical Max. Adsorption (mmol/g) |
|---|---|---|
| A) 30% DS/Ph-A | 0.05 | 0 |
| B) Red. 30% DS/Ph-A | 0.90 | 4.04 |

Disulfide reduction increased $Hg^{+2}$ adsorption of the new material (Red. 30% DS/Ph-A) by 18 times that of the native xerogel (30% DS/Ph-A). However, the resulting adsorption capacity was still well below the theoretical maximum. This indicated that the reduction may have not gone to completion. The $^{13}C$ CP MAS NMR of Red. 30% DS/Ph-A still exhibited chemical shift characteristic of a disulfide bridge which confirmed that reduction was incomplete. Nevertheless, this experiment showed that post-polymerization treatment of disulfide-bridged polysilsesquioxanes could be accomplished and that these modifications can result in significant increase in the mercury (II) adsorption from aqueous solutions.

METHODS OF USE OF THE PRESENT INVENTION

Method of Removing Liquid Contaminants

Contamination occurring in liquid solutions is also a serious concern to society today. In particular, disposing of wastewater is not only very expensive and time consuming, but also extremely harmful to the environment. Some areas of concern in the disposal of wastewater include negatively charged metals such as arsenic, molybdenum, and chromium; positively charged heavy metals such as copper, cadmium, nickel, lead, and zinc; and contaminants such as ammonia, mercury, arsenic and iron.

Chemical procedures have attempted to cause a predetermined reaction between chemical additives and impurities contained within the waste stream. The most common reactions are designed to cause the impurities and the chemical additives to coagulate, wherein the particles increase in size and then separate by either floating on or settling below the treated water. Physical procedures are designed to achieve similar results as chemical additive procedures, but to a lesser degree of purity in the final liquid solution. Filters, centrifuges, plate separators, and clarifiers are the most common physical procedures employed to remove contaminants from aqueous solutions.

The contaminants that may be removed by use of the present invention include an alkali metal compound, an alkali earth metal compound, a transition metal compound, a group III–VIII compound, a lanthanide compound, or an actinide compound. In addition, the contaminants can comprise a copper compound, a chromium compound, a mercury compound, a lead compound, a zinc compound, or an arsenic compound.

The dipropylenedisulfide-co-phenylene-bridged polysilsesquioxanes, and derivatives and analogs thereof, disclosed in the present invention can be utilized with the methods outlined above to remove contaminants, and specifically to remove heavy metal ions, from a liquid solution. In a preferred embodiment of the present invention, this can be done by packing the dipropylenedisulfide-co-phenylene-bridged polysilsesquioxanes, or derivatives and analogs thereof, in a chamber, wherein a housing of the chamber has an inlet and an outlet port. Then, the fluid having the contaminants is passed through the inlet port to the chamber and the adsorbent material containing the dipropylenedisulfide-co-phenylene-bridged polysilsesquioxanes, or derivatives and analogs thereof, to the outlet port, wherein at least a portion of the contaminants are retained by the adsorbent. The fluid may be a liquid or a gas.

An alternative embodiment of the method for precipitating contaminants from an liquid solution, namely wastewater, comprises the steps of: (a) providing an aqueous solution containing contaminants, (b) providing a closed reservoir having an inlet and an outlet, (c) introducing the aqueous solution into the reservoir, (d) injecting a fine white powder into the aqueous solution, wherein the powder comprises dipropylenedisulfide-co-phenylene-bridged polysilsesquioxanes, (e) entraining the dipropylenedisulfide-co-phenylene-bridged polysilsesquioxanes into the liquid solution, (f) passing the liquid solution and the dipropylenedisulfide-co-phenylene-bridged polysilsesquioxanes to a mixer, wherein the mixer contacts the dipropylenedisulfide-co-phenylene-bridged polysilsesquioxanes with the liquid solution to produce a solution—dipropylenedisulfide-co-phenylene-bridged polysilsesquioxanes mixture, (g) selectively inducing a pressure discontinuity extraneous of the reservoir to flocculate contaminants into a separate phase from the aqueous solution, and finally (h) filtering out the dipropylenedisulfide-co-phenylene-bridged polysilsesquioxanes containing the contaminants.

Method of Removing Gaseous Contaminants

The removal of atmospheric contaminants in industrial, commercial, or residential environments is a problem that is becoming more serious each year. Environmental control agencies are implementing increasingly stringent regulations to control emissions, and it is hence becoming more important to comply with environmental emissions standards. Current processes for the removal of atmospheric contaminants include incineration, adsorption, impingement, electrostatic attraction, centrifugation, sonic agglomeration, and ozonization.

The present invention provides a method for continuously removing airborne particulate material and organic vapors from a polluted air stream. For example, the method can be employed in manufacturing facilities where solvents are made and the air is re-circulated, in laboratory hood exhausts, in electroplating operations, and other industrial emission sources. Dipropylenedisulfide-co-phenylene-bridged polysilsesquioxane, and derivatives and anologs thereof, can be used in an apparatus to adsorb contaminants from an exhaust stream. The contaminants can then be converted into harmless chemical substances which can be recovered or easily disposed. The dipropylenedisulfide-co-phenylene-bridged polysilsesquioxane, and derivatives and analogs thereof, can be packed into a column or canister to permit flow through a filter. This could then serve as a component of a filtering system for air supply in an industrial, commercial, or residential setting.

In a preferred embodiment of the present invention, a method of removing airborne particulate material and organic compounds from a polluted air stream comprises the steps of: collecting from an air stream, by filtration and adsorption, particulate material and organic vapors, thus forming an essentially pollutant-free effluent. Next, the collected particulate matter and collected organic vapors are (simultaneously) burned and desorbed, thus forming a concentrated stream comprising combustion products of particulate material and desorbed vapors. The desorbed vapors of the concentrated stream are then oxidized to form an essentially pollution-free oxidized stream comprising both particulate material combustion products and vapor combustion products. The essentially pollutant-free effluent of step (1) and the essentially pollutant-free oxidized stream of step (3) are separately exhausted, resulting in an essentially pollutant-free air stream. Finally, the adsorption of step (1) further comprises the step of passing the air stream across an adsorbent material comprising a dipropylenedisulfide-co-phenylene-bridged polysilsesquioxane, or derivatives and analogs thereof.

The apparatus that such a method to remove contaminants from an air stream comprises: (a) a housing having an inlet for introduction of a polluted air stream, (b) a filtering and adsorption station located within the housing, and having connecting means therefrom to an outlet for exhausting the resultant pollutant-free air stream, and (c) a combustion and desorption station for combustion of particulate matter and desorption of organic compounds, (d) oxidizing means for converting the desorbed vapors into oxidized pollutant-free products, (e) connecting means for providing passage for the resultant combustion products and desorbed vapors from the combustion and desorbing station to the oxidizing means, (f) connecting means for providing passage for the combustion and oxidized products from the oxidizing means to the atmosphere, or alternatively, back to the inlet.

Method of Removing Soil Contaminants

Soil contamination is another environmental problem that is of great concern today. In particular, the removal of contaminants such as organic compounds and heavy metals from the soil is the focus of much research. The contamination of groundwater and, ultimately, drinking water is the driving force behind the extensive research being conducted in order to remove toxic and hazardous contaminants from the soil.

Numerous techniques for the decontamination of soil are disclosed in the art. One approach involves the excavation of soil followed by treating the soil with additives and chemicals to remove the contaminant. Another method involves the addition of additives or chemicals directly into the soil in order to convert the contaminant into a non-leachable form. The contaminant is rendered nonhazardous, and is not removed from the soil. Still another method to treat excavated soil is in situ soil remediation. This process involves contacting the soil with an aqueous extraction solution, directing the extractant solution through the soil so that the extractant solution interacts with the contaminant, and collecting the extractant solution containing the contaminant.

The compounds disclosed in the present invention can be utilized in conjunction with all the methods of removing a contaminant from the soil mentioned above. Specifically, a solution of the monomer mercaptopropyltriethoxysilane can be injected into the ground water. This solution of monomer homopolymerizes in situ, forming a porous seal, thus allowing for the adsorption of contaminants, such as mercury and chromium, that one would not want to spread further into the ground.

Additional contaminants that may be removed from the soil by the methods and compounds disclosed in the present invention comprise an alkali metal compound, an alkali earth metal compound, a transition metal compound, a group III–VIII compound, a lanthanide compound, or an actinide compound, a copper compound, a lead compound, a zinc compound, or an arsenic compound.

In a preferred embodiment of the present invention, a method for removing a contaminant in situ from soil containing the contaminant comprises the steps of: (1) contacting the soil containing the contaminant in situ with a solution of the monomer mercaptopropyltriethoxysilane, or a derivative or analog thereof, to remove the contaminant from the soil and to form a mixture comprising the contaminant. The soil may be contacted by the monomer solution by injection, gallery infiltration, basin infiltration, trench infiltration, surface infiltration, irrigation, spray, flooding, a sprinkler, a leach field, a vertical well, or a horizontal well. (2) Then, a floc is formed in the mixture to form a contaminant-floc complex. This mixture containing the contaminant-floc complex can then be filtered with a suitable filtering apparatus, wherein the mixture is removed from the soil by a recovery well. In an alternative embodiment, the contaminant-floc complex may be left in the ground, as the seal formed by the homopolymerization of the monomer will prevent it from spreading further in the ground.

EXAMPLES

The following examples are put forth so as to provide those of ordinary skill in the art with a complete disclosure and description of how the methods claimed herein are evaluated, and are intended to be purely exemplary of the invention and are not intended to limit the scope of what the inventors regard as their invention. Efforts have been made to ensure accuracy with respect to numbers (e.g., amounts, temperature, etc) but some errors and deviations should be accounted for. Unless indicated otherwise, parts are parts by weight, temperature is in degrees Celcius or is at ambient temperature and pressure is at or near atmospheric.

Example 1

Instrumentation. $^1$H NMR spectra were recorded on a General Electric GN-500 (500 MHz), Omega-500 (500 MHz), Brucker Avance DRX (500 MHz) or GE NR-300 (300 MHz) spectrometer. Chemical shifts are reported on the δ scale in ppm relative to either tetramethylsilane (0.00 ppm) or $CDCl_3$ (7.26 ppm) as internal standard. Coupling constants (J) are reported in Hz; abbreviations are as follows: s, singlet; d, doublet; t, triplet; q, quartet; m, multiplet; br, broad; and refer to the appropriate couplings.

$^{13}$C NMR spectra were recorded on a General Electric GN-500 (125 MHz), Brucker Avance DRX (125 MHz) or Omega-500 (125 MHz) spectrometer. Chemical shifts are reported in ppm relative to either tetramethylsilane (0.00 ppm), $CDCl_3$ (77.0 ppm) as an internal standard. $^{29}$Si NMR spectra were obtained on the Omega-500 (99 MHz) or General Electric GN-500 (99 MHz) spectrometer with tetramethylsilane (0.00 ppm) as external or internal standard.

$^{13}$C and $^{29}$Si Solid State NMR were obtained on a Chemagnetics CMX-200 spectrometer at 50.29 MHz and 39.73 MHz, respectively. Hexamethylbenzene (HMB) was used as an external standard (17.53 ppm relative to TMS) for $^{13}$C; hexamethylcyclotrisiloxane (HMTS) used as external standard (−9.33 ppm relative to TMS) for $^{29}$Si. Cross polarization experiments were conducted with an optimum contact time of 3.0–5.0 ms for both nuclei. The number of acquisitions were 2000 for $^{29}$Si and $^{13}$C with a recycle delay of 1 second. Single pulse experiments were conducted for $^{13}$C and $^{29}$Si in order to verify and quantify peak assignments. Recycle delay times were 30 and 180 seconds respectively. $^{13}$C interrupted decoupling experiments were utilized to verify carbon assignments with optimum acquisition delay times (τ=50 to 150 ms). Sample spinning rates were 3.0–4.0 KHz for $^{29}$Si and $^{13}$C nuclei.

Infra-red spectra were recorded on a Analect RFX-40 FTIR spectrophotometer. High resolution mass spectra were obtained with a VG-7070e high resolution mass spectrometer or Fisons Autospec mass spectrometer and are reported as mass/charge (m/z) ratios using chemical ionization (CI, isobutane or $NH_3$) or electron ionization (EI, 70 eV) with percent relative abundance Surface area measurements were made on a Micromeritics ASAP 2000 porosimeter using high purity nitrogen as adsorbate at 77 K. Surface areas were calculated by the BET equation (0.05 $P/P_0$ 0.35 for $N_2$) and pore distributions characterized by Barret-Joyner-Halendg. Thermal analyses were recorded on a DuPont Thermal Analyst 2000 with 910 DSC and 951 TGA modules. A 10° C./min heating ramp was used with a constant flow of $N_2$ (80 mL/min). Indium and zinc were used as external calibrants for the DSC while indium and silver were used for the TGA. Elemental analyses were performed by Galbraith Laboratories, Inc., Knoxville, Tenn.

Monomer Preparation

Example 2

1,4-bis(triethoxysilyl)benzene. A mixture of magnesium turnings (15 g) and TEOS (450 mL, 2 mol) in THF (300 mL) were placed under nitrogen in a 1 L three-neck round bottom flask equipped with magnetic stir bar, condenser, and addition funnel. A small crystal of iodine was added and the mixture was brought to reflux. A solution of 1,4-dibromobenzene (48 g, 204 mmol) in THF (100 mL) was added dropwise over 2 h. Within 30 min of initiating the addition, the reaction became mildly exothermic. The reaction mixture was kept at reflux for 1 h after the completion of the addition of dibromide. The gray-green mixture was allowed to cool to room temperature before the THF was removed in vacuo. Hexane (200 mL) was added to precipitate any remaining magnesium salts in solution and the mixture was quickly filtered under nitrogen to produce a clear, light brown solution. Hexane was removed in vacuo. The product was purified by fractional distillation. The product was recovered as a clear liquid at 130–5° C. (0.2 mmHg) in 43–47% yield. $^1$H NMR (500 MHz, $CDCl_3$) δ 7.67 (s, 4H, ArH), 3.86 (q, J=7.00 Hz, 12H, $OCH_2CH_3$), 1.23 (t, J=7.00 Hz, 18H, ArH); $^{13}$C NMR (125 MHz, $CDCl_3$) δ 133.25, 57.98, 17.43; $^{29}$Si NMR (99 MHz, $CDCl_3$) δ−58.25; MS m/e calc'd for CI (M) $C_{18}H_{34}Si_2O_6$: 402.1894, found 402.1886.

Example 3

Bis(triethoxysilyl)propyl disulfide (via bromine coupling). An oven dried 3-neck flask was equipped with a stir bar, nitrogen inlet, an outlet to an acid trap (saturated aqueous $NaHCO_3$), and a septum. To the flask was added 3-mercaptopropyltriethoxysilane (26.8 mL, 104.9 mmol). Bromine (2.7 mL, 52.4 mmol, 0.5 eq) was added drop wise over 10 minutes and the orange solution was stirred for 10 minutes with the concomitant evolution of HBr. To the reaction mixture, THF (150 mL) was added. The addition funnel was charged with a solution of ethanol (26.6 mL) and diisopropylethylamine (69 mL). The red solution was cooled to 0° C. and the EtOH/(i-Pr)$_2$NEt solution was added drop wise over 15 minutes and the solution was allowed to warm to ambient temperature and stirred overnight. The reaction mixture was then refluxed for 4 h. The reaction mixture was cooled to 0° C. and the amine salts were removed by filtration. The solvent, THF, was removed in vacuo, and residual salts were precipitated by the addition of dry hexane. Final filtration and removal of volatile organics in vacuo yielded a pale yellow oil. Final purification was accomplished by chromatography (10/1 petroleum ether/ether, $R_F$=0.25) to give a clear, colorless oil in 33% yield. $^1$H NMR (500 MHz, $CDCl_3$) δ3.80 (q, J=7.0 Hz, 12H, Si(OCH$_2$CH$_3$), 2.69 (t, J=7.3 Hz, 4H, SCH$_2$), 1.80 (m, 4H, SCH$_2$CH$_2$), 1.22 (t, J=7.0 Hz, 18H, Si(OCH$_2$CH$_3$), 0.72 (m, 4H, SCH$_2$ CH$_2$CH$_2$; $^{13}$C NMR (125 MHz, $CDCl_3$) δ 58.6, 42.0, 22.8, 18.5, 9.6; $^{29}$Si NMR (99 MHz, $CDCl_3$) δ−45.87; MS m/e calc'd for CI (M) $C_{18}H_{42}Si_2O_6S_2$: 474.1961, found 474.1960

Example 4

Bis(triethoxysilyl)propyl disulfide (oxidative coupling w/ $SO_2Cl_2$). To a 3-neck flask was added 3-mercaptopropyltriethoxysilane (15.1 mL, 59 mmol) and 1,2-dichloroethane (25 mL). Under a steady stream of nitrogen, a reflux condenser was added. A nitrogen inlet was fitted such that $N_2$ can be bubbled in a steady stream through the clear solution to an outlet acid trap. Freshly distilled $SO_2Cl_2$ (2,6 mL, 32.5 mmol,) was added in portions over 15 minutes. Upon initial addition, a white precipitate developed which disappeared after ~90% of the $SO_2Cl_2$ had been added. After all the $SO_2CL_2$ had been added, HCl evolution was evident. The yellow solution was stirred at ambient temperature for 10 minutes, heated to reflux, and allowed to react for 2 hours. To the reaction mixture, THF (60 mL) was added. An addition funnel was fitted to the reaction flaske and charged with a solution of ethanol (10.4 mL) and triethylamine (21.5 mL). The red solution was cooled to 0° C. and the EtOH/Et$_3$N solution was added drop wise over 15 minutes and the solution was allowed to warm to ambient temperature and stirred overnight. The reaction mixture was then refluxed for 4 h. The reaction mixture was cooled to 0° C. and the amine salts were removed by filtration. The solvent, THF, was removed in vacuo, and residual salts were precipitated by the addition of dry hexane. The reaction was filtered and then concentrated in vacuo to provide the clear liquid product in 95% yield. $^1$H NMR (500 MHz, $CDCl_3$) δ 3.80 (q, J=7.0 Hz, 12H, Si(OCH$_2$CH$_3$), 2.69 (t, J=7.3 Hz, 4H, SCH$_2$), 1.80 (m, 4H, SCH$_2$CH$_2$), 1.22 (t, J=7.0 Hz, 18H, Si(OCH$_2$CH$_3$), 0.72 (m, 4H, SCH$_2$ CH$_2$CH$_2$; $^{13}$C NMR (125 MHz, $CDCl_3$) δ 58.6, 42.0, 22.8, 18.5, 9.6; $^{29}$Si NMR (99 MHz, $CDCl_3$) δ−45.87; MS m/e calc'd for CI (M) $C_{18}H_{42}Si_2O_6S_2$: 474.1961, found 474.1960.

Sol-Gel Polymerizations

Example 5

Mercaptopropylene/Phenylene Xerogels Sol-gel materials containing 3-mercaptopropyltriethoxysilane and 1,4-bis(triethoxysilyl)benzene were prepared under both acid and base catalyzed conditions. The gels were hydrolitically condensed using 0.4M monomer solutions in ethanol, 6:1 mole ratio of water to monomer, and 10.8 mol % of catalyst (1N HCl or 1N NaOH). Polymerizations were carried out at room temperature in capped polyethylene bottles. After gelation, the gels were aged for twice the gelation time by allowing to stand at room temperature. The crushed gels were soaked in water overnight, filtered, and air-dried for 2 days. The xerogels were ground into fine white powders and dried under vacuum. An example of a typical formulation is shown below.

Example 6

80% Mercaptopropylene/Phenylene Xerogel (0.4M ; total volume 15 mL) 3-mercaptopropyltriethoxysilane (1.144 g, 1.144 mL, 4.8 mmol) and 1, 4-bis(triethoxysilyl)benzene (0.483 g, 483.17 mL, 1.2 mmol) were placed in a 25-mL polypropylene bottle. Ethanol (9.989 g, 12.725 mL) was added to the bottle and the reaction mixture was swirled to insure mixing. The catalyst, 1N HCl (0.648 g, 648 uL) or 1N NaOH (0.648 g, 648 uL), was added in one portion to the reaction bottle. The bottle was capped, shaken vigorously for 1 minute, and allowed to stand at room temperature until gelation occurred. After aging for 1 week, the gel was removed from the bottle and crushed into smaller sections using a spatula. The gel washed with EtOH and soaked in water overnight. Water was removed from the gel by filtration with slight vacuum and air dried for several days. The gel was then grounded into a powder and dried further by heating(100° C.) under high vacuum overnight.

Example 7

60% Mercaptopropylene/Phenylene Xerogel (0.4M; total volume 15 mL) 3-mercaptopropyltriethoxysilane (0.858 g, 858.31 uL, 3.6 mmol); 1,4-bis(triethoxysilyl)benzene (0.966 g, 966.34 uL, 2.4 mmol); 1N HCl (0.648 g, 648 uL) or 1N NaOH (0.648 g, 648 uL); ethanol (9.834 g, 12.527 mL).

Example 8

40% Mercaptopropylene/Phenylene Xero gel (0.4M ;total volume 15 mL) 3-mercaptopropyltriethoxysilane (0.572 g, 572.21 uL, 2.4 mmol); 1,4-bis(triethoxysilyl)benzene (1.449 g, 1.450 mL, 3.6 mmol); 1N HCl (0.648 g, 648 uL) or 1N NaOH (0.648 g, 648 uL); ethanol (9.524 g, 12.133 mL).

Example 9

20% Mercaptopropylene/Phenylene Xerogel (0.4M ; total volume 15 mL) 3-mercaptopropyltriethoxysilane (0.286 g, 286.10 uL, 1.2 mmol); 1,4-bis(triethoxysilyl)benzene (1.932 g, 1.932 mL, 4.8 mmol); 1N HCl (0.648 g, 648 uL) or 1N NaOH (0.648 g, 648 uL); ethanol (9.447 g, 12.035 mL).

Example 10

Dipropylenedisulfide/Phenylene Xerogels Dipropylenedisulfide/phenylene xerogels were prepared under the same conditions used for mercaptopropylene/henylene xerogels. Sol-gel materials containing bis(3-triethoxysilyl)propyl disulfide and 1,4-bis(triethoxysilyl)benzene were prepared under both acid and base catalyzed conditions. The gels were hydrolitically condensed using 0.4M monomer solutions in ethanol, 6:1 mole ratio of water to monomer, and 10.8 mol % of catalyst (1N HCl or 1N NaOH). Polymerizations were carried out at room temperature in capped polyethylene bottles. After gelation, the gels were aged for twice the gelation time by allowing to stand at room temperature. The crushed gels were soaked in water overnight, filtered, and air-dried for 2 days. The xerogels were ground into fine white powders and dried under vacuum. An example of a typical formulation is shown below.

Example 11

80% Dipropylenedisulfide/Phenylene Xerogel (0.4M; total volume 25 mL) bis(3-triethoxysilyl)propyl disulfide (3.798 g, 3.798 mL, 8 mmol) and 1,4-bis(triethoxysilyl) benzene (0.805 g, 805.28 uL, 2 mmol) were placed in a 25-mL polypropylene bottle. Ethanol (19.316 mL) was added to the bottle and the reaction mixture was swirled to insure mixing. The catalyst, 1N HCl (1.08 g, 1.08 mL) or 1N NaOH (1.08 g, 1.08 mL), was added in one portion to the reaction bottle. The bottle was capped, shaken vigorously for 1 minute, and allowed to stand at room temperature until gelation occurred. After aging for 1 week, the gel was removed from the bottle and crushed into smaller sections using a spatula. The gel washed with EtOH and soaked in water overnight. Water was removed from the gel by filtration with slight vacuum and air dried for several days. The gel was then grounded into a powder and dried further by heating(100° C.) under high vacuum overnight. $^{13}$C NMR (125 MHz, CDCl$_3$) δ 134, 38, 20, 9.

Example 12

60% Dipropylenedisulfide/Phenylene Xerogel (0.4M ; total volume 25 mL) bis(3-triethoxysilyl)propyl disulfide (2.849 g, 2.849 mL, 6 mmol); 1,4-bis(triethoxysilyl)benzene (1.611 g, 1.611 mL, 4 mmol); 1N HCl (1.08 g, 1.08 mL) or 1N NaOH (1.08 g, 1.08 mL); ethanol (19.461 mL).

Example 13

40% Dipropylenedisulfide/Phenylene Xerogel (0.4M ; total volume 25 mL) bis(3-triethoxysilyl)propyl disulfide (1.899 g, 1.899 mL, 4 mmol); 1,4-bis(triethoxysilyl)benzene (2.416 g, 2.416 mL, 6 mmol); 1N HCl (1.08 g, 1.08 mL) or 1N NaOH (1.08 g, 1.08 mL); ethanol (19.605 mL).

Example 14

20% Dipropylenedisulfide/Phenylene Xerogel (0.4M; total volume 25 mL) bis(3-triethoxysilyl)propyl disulfide (.950 g, 950 uL, 2 mmol); 1,4-bis(triethoxysilyl)benzene (3.221 g, 3.221 mL, 8 mmol); 1N HCl (1.08 g, 1.08 mL) or 1N NaOH (1.08 g, 1.08 mL); ethanol (19.749 mL).

Example 15

100% Dipropylenedisulfide/Phenylene Xerogel (0.4M; total volume 20 mL) bis(3-triethoxysilyl)propyl disulfide (3.799 g, 3.799 mL, 8 mmol); 1N HCl (0.864 g, 864 uL) or 1N NaOH (0.864 g, 864 uL); ethanol (15.337 g, 12.04 mL).

Example 16

Hg$^{+2}$ Uptake Experiments. Mercury(II) nitrate in water was used as the Hg$^{+2}$ source. The experiment consisted of taking 10 mg portions of the doped materials and stirring for 18–24 hours at room temperature with 50 mL volumes of Hg(NO$_3$)$_2$ solutions at initial concentrations that ranged from 0–300 ppm. The solutions were stirred in amber bottles. Mercury(II) concentrations were determined before and after treatment by colormetric analysis using diphenylthiocarbazone as indicator.[14] Calibration for the colorimetric analysis was preformed using Hg(NO$_3$)$_2$ standards that ranged from 0–300 ppm. All solutions were filtered through 0.2–0.5 um syringe filters before colorimetric analysis.

Reduction of Disulfide Bridged Xerogels

Example 17

Reduced 80% Dipropylenedisulfide/Phenylene Xerogel. 80% DS/Ph-A (1 g, 4.2 mmol), 10% methanol (100 mL), and tri-n-butyl phosphine (3.40 g, 16.8 mmol) were placed in a reaction flask equipped with a reflux condenser. The hetereogenous reaction was allowed to stir at reflux for 3 days under nitrogen atmosphere. The reaction was cooled to room temperature and filtered. The solid was washed consecutively with 200 mL portions of 10% MeOH, H$_2$O, and acetone. The solid was collected by filtration and dried under high vacuum at 100° C. overnight. $^{13}$C NMR (125 MHz, CDCl$_3$) δ 134, 27, 16, 11.

Example 18

Reduced 30% Dipropylenedisulfide/Phenylene Xerogel. 30% DS/Ph-A (0.5 g, 0.74 mmol), 10% methanol (100 mL), and tri-n-butyl phosphine (1.49 g, 1.15 mmol) were placed in a reaction flask equipped with a reflux condenser. The hetereogenous reaction was allowed to stir at reflux for 3 days under nitrogen atmosphere. The reaction was cooled to room temperature and filtered. The solid was washed consecutively with 200 mL portions of 10% MeOH, H$_2$O, and acetone. The solid was collected by filtration and dried under high vacuum at 100° C. overnight.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of removing contaminants from a fluid, comprising the steps of:
    providing a housing having an inlet port that communicates with a chamber and an outlet port that communicates with the chamber, the chamber containing an adsorbent material comprising a dipropylenedisulfide-co-phenylene-bridged polysilsesquioxanes, or derivative or analog thereof;
    passing the fluid having contaminants through the inlet port and the adsorbent material contained in the chamber; and
    passing the fluid through the outlet port,
    wherein at least a portion of the contaminants are retained by the adsorbent material.

2. The method of claim 1, wherein the fluid is a gas.

3. The method of claim 1, wherein the fluid is a liquid.

4. The method of claim 1, wherein the dipropylenedisulfide-co-phenylene-bridged polysilsesquioxanes has the formula

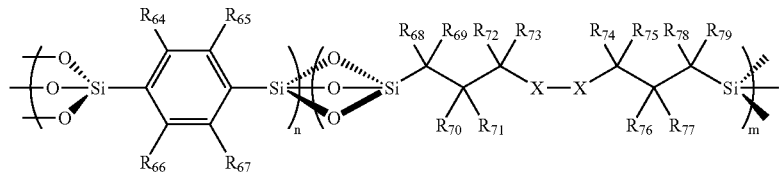

wherein:
    n is one or larger; and
    m is one or larger; and
    R$_{64}$–R$_{67}$ are independently selected from the group consisting of hydrogen, C$_1$–C$_n$ straight or branched chain alkyl, C$_1$–C$_n$ straight or branched chain alkenyl, wherein n is greater than one; aryl, C$_3$–C$_8$ cycloalkyl, C$_5$–C$_7$ cycloalkenyl, benzyl, phenyl, halides, ethers, alcohols, sulfides, amines, nitro, nitrile, azide, and a heterocycle;
    R$_{68}$–R$_{79}$ are independently selected from the group consisting of hydrogen, C$_1$–C$_n$ straight or branched chain alkyl, C$_1$–C$_n$ straight or branched chain alkenyl, wherein n is greater than one; aryl, C$_3$–C$_8$ cycloalkyl, C$_5$–C$_7$ cycloalkenyl, benzyl, phenyl, halides, ethers, alcohols, sulfides, amines, nitro, nitrile, azide, and a heterocycle; and
    wherein X is selected from the group consisting of sulfur, oxygen, nitrogen, phosphorus, selenium, and boron, or wherein X—X is selected from the group consisting of anhydrides, or phosphorus anhydrides.

5. The method of claim 4, wherein the halides selected from the group consisting of flourine, chlorine, bromine, and iodine.

6. The method of claim 4, wherein the heterocycle is selected from the group consisting of 2-pyridyl, 3-pyridyl, 4-pyridyl, furan, and thiophene.

7. The method of claim 4, wherein the ethers are of the general formula —O—R$_{80}$ wherein R$_{80}$ is independently selected from the group consisting of C$_1$–C$_n$ straight or branched chain alkyl, C$_1$–C$_n$ straight or branched chain alkenyl, wherein n is greater than one; aryl, C$_3$–C$_8$ cycloalkyl, C$_5$–C$_7$ cycloalkenyl, benzyl, phenyl, and a heterocycle.

8. The method of claim 7, wherein the heterocycle is selected from the group consisting of 2-pyridyl, 3-pyridyl, 4-pyridyl, furan, and thiophene.

9. The method of claim 4, wherein the amines are of the general formula —N(—R$_{81}$)—R$_{82}$, wherein R$_{81}$ and R$_{82}$ are independently selected from the group consisting of hydrogen, C$_1$–C$_n$ straight or branched chain alkyl, C$_1$–C$_n$ straight or branched chain alkenyl, wherein n is greater than one; aryl, C$_3$–C$_8$ cycloalkyl, C$_5$–C$_7$ cycloalkenyl, benzyl, phenyl, and a heterocycle.

10. The method of claim 9, wherein the heterocycle is selected from the group consisting of 2-pyridyl, 3-pyridyl, 4-pyridyl, furan, and thiophene.

11. A method for precipitating and/or removing contaminants from an aqueous solution comprising the steps of:
    (a) providing an aqueous solution containing contaminants;
    (b) providing a closed reservoir having an inlet and an outlet;
    (c) introducing the aqueous solution into the reservoir;
    (d) injecting a fine white powder into the aqueous solution, wherein the powder comprises dipropylenedisulfide-co-phenylene-bridged polysilsesquioxanes;
    (e) entraining the dipropylenedisulfide-co-phenylene-bridged polysilsesquioxanes into the aqueous solution;
    (f) passing the aqueous solution and the dipropylenedisulfide-co-phenylene-bridged polysilsesquioxanes to a mixer, wherein the mixer contacts the dipropylenedisulfide-co-phenylene-bridged polysilsesquioxanes with the aqueous solution to produce a solution—dipropylenedisulfide-co-phenylene-bridged polysilsesquioxanes mixture;
(g) selectively inducing a pressure discontinuity extraneous of the reservoir to flocculate contaminants into a separate phase from the aqueous solution;
(h) filtering out the dipropylenedisulfide-co-phenylene-bridged polysilsesquioxanes containing the contaminants.

12. The method of claim 11, wherein the contaminant comprises an alkali metal compound, an alkali earth metal compound, a transition metal compound, a group III–VIII compound, a lanthanide compound, or an actinide compound.

13. The method of claim 11, wherein the contaminant comprises a copper compound, a chromium compound, a mercury compound, a lead compound, a zinc compound, or an arsenic compound.

14. The method of claim 11, wherein the dipropylenedisulfide-co-phenylene-bridged polysilsesquioxanes is made by the following steps: polymerizing 1,4-bis-(triethoxysilyl)benzene or a derivative or analog thereof, with at least one of mercaptopropyltriethoxysilane or a derivative or analog thereof, or bis-(3-triethoxysilylpropyl)disulfide or a derivative or analog thereof, to produce dipropylenedisulfide-co-phenylene-bridged polysilsesquioxanes, or a derivative or analog thereof.

15. The method of claim 11, wherein the dipropylenedisulfide-co-phenylene-bridged polysilsesquioxanes, and derivatives and analogs thereof is made by the following steps: the polymerzing of 1,4-bis-(triethoxysilyl)benzene, and derivatives and analogs thereof, and mercaptopropyltriethoxysilane, and derivatives and analogs thereof, is performed using 1,4-bis-(triethoxysilyl)benzene, and derivatives and analogs thereof, and mercaptopropyltriethoxysilane, or derivatives or analogs thereof, in a ratio selected from the group consisting of:
(a) 90% 1,4-bis-(triethoxysilyl)benzene, or derivatives and analogs thereof: 10% mercaptopropyltriethoxysilane, or derivatives and analogs thereof;
(b) 80% 1,4-bis-(triethoxysilyl)benzene, or derivatives and analogs thereof: 20% mercaptopropyltriethoxysilane, or derivatives and analogs thereof;
(c) 60% 1,4-bis-(triethoxysilyl)benzene, or derivatives and analogs thereof: 40% mercaptopropyltriethoxysilane, or derivatives and analogs thereof;
(d) 40% 1,4-bis-(triethoxysilyl)benzene, or derivatives and analogs thereof: 60% mercaptopropyltriethoxysilane, or derivatives and analogs thereof; or
(e) 20% 1,4-bis-(triethoxysilyl)benzene, or derivatives and analogs thereof: 80% mercaptopropyltriethoxysilane, or derivatives and analogs thereof.

16. The method of claim 11 wherein the dipropylenedisulfide-co-phenylene-bridged polysilsesquioxanes, and derivatives and analogs thereof is made by the following steps: the polymerizing of 1,4-bis-(triethoxysilyl)benzene, or derivatives and analogs thereof, and bis-(3-triethoxysilylpropyl)disulfide, derivatives and analogs thereof, is performed using 1,4-bis-(triethoxysilyl)benzene, or derivatives and analogs thereof, and bis-(3-triethoxysilylpropyl)disulfide, or derivatives and analogs thereof in a ratio selected from the group consisting of:
(a) 80% 1,4-bis-(triethoxysilyl)benzene, or derivatives and analogs thereof: 20% bis-(3-triethoxysilylpropyl)disulfide or derivatives and analogs thereof;
(b) 60% 1,4-bis-(triethoxysilyl)benzene, or derivatives and analogs thereof: 40% bis-(3-triethoxysilylpropyl)disulfide, or derivatives and analogs thereof;
(c) 40% 1,4-bis-(triethoxysilyl)benzene, or derivatives and analogs thereof: 60% bis-(3-triethoxysilylpropyl)disulfide, or derivatives and analogs thereof;
(d) 20% 1,4-bis-(triethoxysilyl)benzene, or derivatives and analogs thereof: 80% bis-(3-triethoxysilylpropyl)disulfide, or derivatives and analogs thereof; or
(e) 0% 1,4-bis-(triethoxysilyl)benzene, or derivatives and analogs thereof: 100% bis-(3-triethoxysilylpropyl)disulfide, or derivatives and analogs thereof.

* * * * *